United States Patent
Jiang et al.

(10) Patent No.: US 10,342,413 B2
(45) Date of Patent: Jul. 9, 2019

(54) SHEATHED DUODENOSCOPE

(71) Applicants: Kerang Jiang, Shenyang (CN);
Xiangyang Wu, Shenyang (CN);
Zhenyu Zhou, Shenyang (CN); Chong Chen, Shenyang (CN); Jian Zhang, Shenyang (CN); Ming Xu, Shenyang (CN)

(72) Inventors: Kerang Jiang, Shenyang (CN);
Xiangyang Wu, Shenyang (CN);
Zhenyu Zhou, Shenyang (CN); Chong Chen, Shenyang (CN); Jian Zhang, Shenyang (CN); Ming Xu, Shenyang (CN)

( * ) Notice: Subject to any disclaimer, the term of this patent is extended or adjusted under 35 U.S.C. 154(b) by 106 days.

(21) Appl. No.: 15/098,602

(22) Filed: Apr. 14, 2016

(65) Prior Publication Data
US 2016/0227988 A1    Aug. 11, 2016

(30) Foreign Application Priority Data
Jan. 29, 2016    (CN) .......................... 2016 1 0077150

(51) Int. Cl.
*A61B 1/00*    (2006.01)
*A61B 1/06*    (2006.01)

(52) U.S. Cl.
CPC ...... *A61B 1/00142* (2013.01); *A61B 1/00096* (2013.01); *A61B 1/00098* (2013.01);
(Continued)

(58) Field of Classification Search
CPC ............ A61B 1/00135; A61B 1/00142; A61B 1/00154; A61B 1/00098; A61B 1/0008; A61B 1/00082; A61B 1/00089; A61B 1/00101; A61B 1/0014; A61B 1/00174; A61B 1/00177; A61B 1/00179; A61B 1/012; A61B 1/0125; A61B 1/018; A61B 1/0607; A61B 1/0615; A61B 1/0623; A61B 1/00137; A61B 1/00131
(Continued)

(56) References Cited

U.S. PATENT DOCUMENTS

4,198,959 A    4/1980  Otani
4,646,722 A *  3/1987  Silverstein ......... A61B 1/00073
                                                    600/104
(Continued)

*Primary Examiner* — Ryan N Henderson
(74) *Attorney, Agent, or Firm* — Jeanette Meng Nakagawa (57) ABSTRACT

The present disclosure is for an endoscope assembly comprising an endoscope and a disposable sheath cover. The endoscope comprises an illumination window adjacent to an observation window situated along a lateral side of a distal end portion, and an elongated slot to accommodate biopsy instruments. The sheath further comprises an end cap fitted around the end portion of the endoscope with a capsule secured to its inner wall. When the end cap engages the endoscope, the capsule is ruptured to release a transparent liquid immersing the illumination window and the observation window. A soft connector is bonded to the end cap covering the elongated slot, and to an outer surface of a biopsy channel. The soft connector further comprises an opening allowing the biopsy channel to pass through. The sheath can accommodate air/water tubes, and is secured onto the shaft of the endoscope via a cuff.

8 Claims, 8 Drawing Sheets

(52) U.S. Cl.
CPC ...... *A61B 1/00101* (2013.01); *A61B 1/00135* (2013.01); *A61B 1/00137* (2013.01); *A61B 1/00177* (2013.01); *A61B 1/0615* (2013.01)

(58) Field of Classification Search
USPC ....... 600/104, 106, 107, 121–125, 127, 129, 600/156–159, 170–177
See application file for complete search history.

(56) References Cited

U.S. PATENT DOCUMENTS

| | | | | |
|---|---|---|---|---|
| 5,460,168 | A * | 10/1995 | Masubuchi | ........ A61B 1/00096 600/107 |
| 2004/0077927 | A1 * | 4/2004 | Ouchi | .................... A61B 1/018 600/123 |
| 2004/0267090 | A1 * | 12/2004 | Ueno | .................... A61B 1/0052 600/106 |
| 2007/0246506 | A1 * | 10/2007 | Hamazaki | ............ A61B 1/0008 227/175.1 |
| 2012/0323074 | A1 * | 12/2012 | Iyama | .................... A61B 1/015 600/114 |

* cited by examiner

SHEATHED DUODENOSCOPE

FIELD OF THE INVENTION

An invention in the field of medical device, to be specified, a sheathed endoscope.

BACKGROUND OF THE INVENTION

Duodenoscope is widely used in the diagnosis and treatments of diseases in liver, gall bladder and pancreas, especially as an essential and irreplaceable device for the procedure of Endoscopic retrograde cholangiopancreatography ERCP and minimally invasive surgery. However, inadequate disinfection of duodenoscopes has been a top medical hazard. Autoclave cannot be applied due to the intolerance of the charge—coupled device CCD—a component material of endoscope, to high temperature and pressure. In the operation part, steel wire was used to control the forceps elevator to lift up and down, and the structure is quite complicated with wire leading orifices. The disinfection is inadequate due to disinfection limitations. This patented duodenoscope has even more complicated structure inside and carries more risks than common duodenoscope.

To use disposable material covering the endoscope is the most reliable way to prevent infections of endoscopes, eg. In a Chinese patent 201510461920.8 (application date: Jul. 31, 2015): To use a disposable consumable cover the endoscope to separate all contacting surfaces between patients and endoscope. However, it resulted in compromised image quality due to that stray light is produced as there are gaps between the distal end of endoscope and covering end cap. Based on this patent, we further modified the structure to solve the problem brought by stray light.

SUMMARY OF THE INVENTION

A sheathed endoscope, of which the basic principles are to use sterile disposable consumable material to protect the endoscopes which cannot be autoclaved, through covering all contaminated surfaces and potential exposed areas of endoscopes. Furthermore, this invention also solves the problem of stray light with an anti-stray light design on both of the end cap and the distal end of endoscopes.

TECHNIQUES OF THE INVENTION

An endoscope with sheath, comprising an endoscope and a disposable component wherein an inner surface and an outer surface of the endoscope are protected by the disposable component, and the disposable component comprises an end cap that covers a distal end portion of a shaft of the endoscope, characterized by: a plurality of windows being provided on a side of the distal end portion of the shaft of the endoscope, capsule filled with transparent liquid being provided in between the end cap and the distal end portion of the shaft of the endoscope, the capsule becoming broken under a cooperative action of the end cap and the distal end portion of the shaft of the endoscope, after the capsule being broken, the transparent liquid contained in the capsule filling a space between the end cap and the plurality of windows located in the distal end portion of the shaft of the endoscope.

The disposable component comprises the end cap, a cuff and a disposable biopsy channel, wherein the end cap is covered on the distal end portion of the shaft of the endoscope, the disposable biopsy channel is disposed within the endoscope, the cuff is disposed outside of the endoscope and the cuff is connected to the disposable biopsy channel by way of the end cap. An elongated slot is provided on a side of the end cap, wherein the elongated slot is in a shape consistent with a shape of a surgical channel on the distal end portion of the shaft of the endoscope, a soft connector is disposed in the elongated slot, an outer edge of a large opening of the soft connector is sealingly bonded to an inner side of the elongated slot on the end cap, and a small opening of the soft connector is covered on the disposable biopsy channel.

The endoscope with sheath comprises the distal end portion of the shaft of the endoscope, a forceps elevator and a controlling wire, an opening is provided on a side of the distal end portion of the shaft of the endoscope, the forceps elevator is disposed in the foregoing opening, and the forceps elevator is operable via the controlling wire.

An observation window and an optical illumination window are provided on a side of the distal end portion of the shaft of the endoscope, a light window is provided on a lower side of the end cap at a location corresponding to the locations of the observation window and the optical illumination window on the distal end portion of the shaft of the endoscope, the transparent liquid being filled in a space between the light window on the end cap and the observation window and optical illumination window on the distal end portion of the shaft of the endoscope.

An inclined surface is formed at a location connecting an front end face of the end cap and the lower side of the end cap, a recess is formed on the inclined surface, the capsule is disposed in the recess, another inclined surface is provided on a side of a lateral front end surface of the observation window and the optical illumination window on the distal end portion of the shaft of the endoscope, which is near the lower side of the end cap 2.1, and the capsule is broken by way of a cooperative action of the inclined surface on the distal end portion of the shaft of the endoscope and the inclined surface with the recess on the end cap.

A boss is provided on an inner wall of a front end of the end cap, a hollow needle is provided on a front end of the distal end portion of the shaft of the endoscope, the capsule is disposed on the boss and a puncturable by the hollow needle, a through hole is provided at a tail end of the hollow needle, and the transparent liquid flows to the space between the end cap and the plurality of windows on the distal end portion of the shaft of the endoscope via the through hole. A conical recess is provided on a concentric axis between the distal end portion of the shaft of the endoscope and the capsule, a blind hole is provided at a bottom of the conical recess, the blind hole is communicated with the through hole, the hollow needle is mounted in the blind hole with its pinpoint facing outside, and the pinpoint of the hollow needle is not higher than a large end surface of the conical recess.

Advantages and Positive Effects of the Invention

1. Design to prevent stray light interference, wherein there is a capsule containing transparent fluid, which will become broken under a cooperative action of the end cap and the distal end portion of the shaft of the endoscope, and the transparent liquid contained in the capsule filling a space between the end cap and the distal end portion of the shaft of the endoscope, preventing interference from stray light.

2. All contacting surfaces between endoscope and patient are covered by disposable component, to protect endoscope from cross contamination.

1. Endoscope 1.1 The distal end portion of the shaft of endoscope 1.2 Forceps Elevator. 1.3 Observation window 1.4 Optical illumination window 1.5 Controlling wire 1.6 Hollow needle 2 Disposable Component 2.1 The end cap 2.2 Capsule 2.3 Air/water channel 2.4 Cuff 2.5 Soft connector 2.6 Disposable biopsy channel 2.7 Lower side 2.8 Recess 2.9 Boss 2.10 Through Hole 3 Biopsy forceps

DETAILED DESCRIPTION

Figure 1:
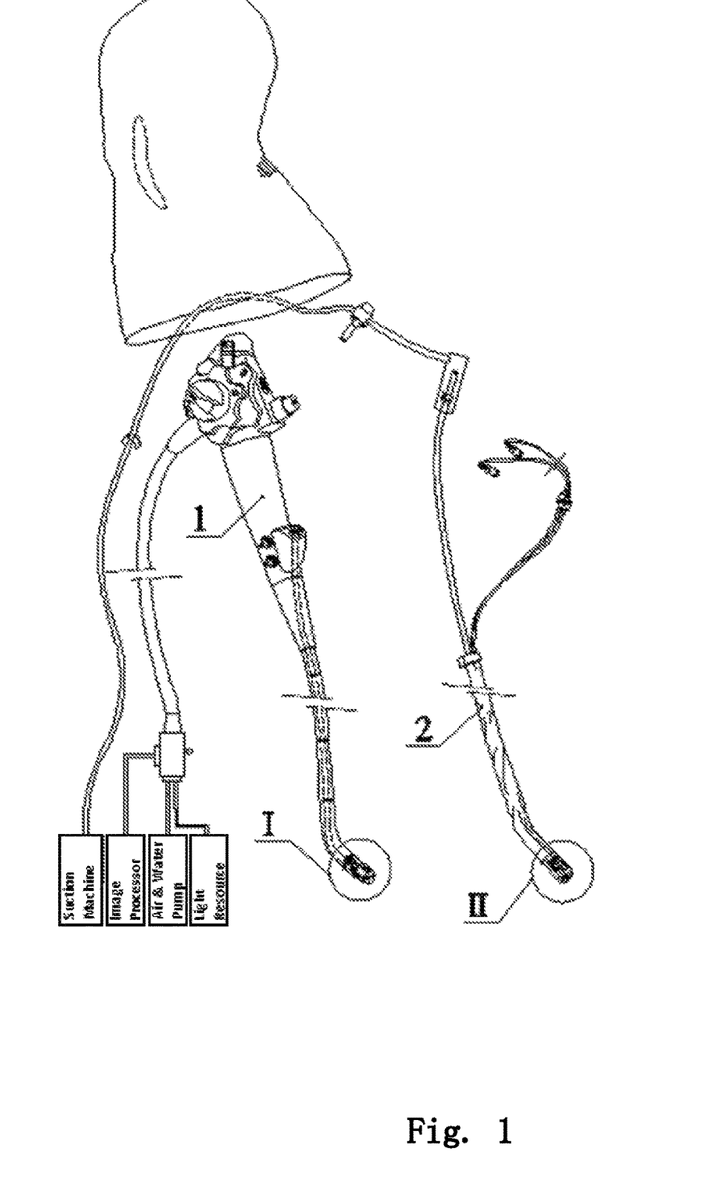
FIG. 1 is a display of components of endoscope with sheath.
Figure 2:
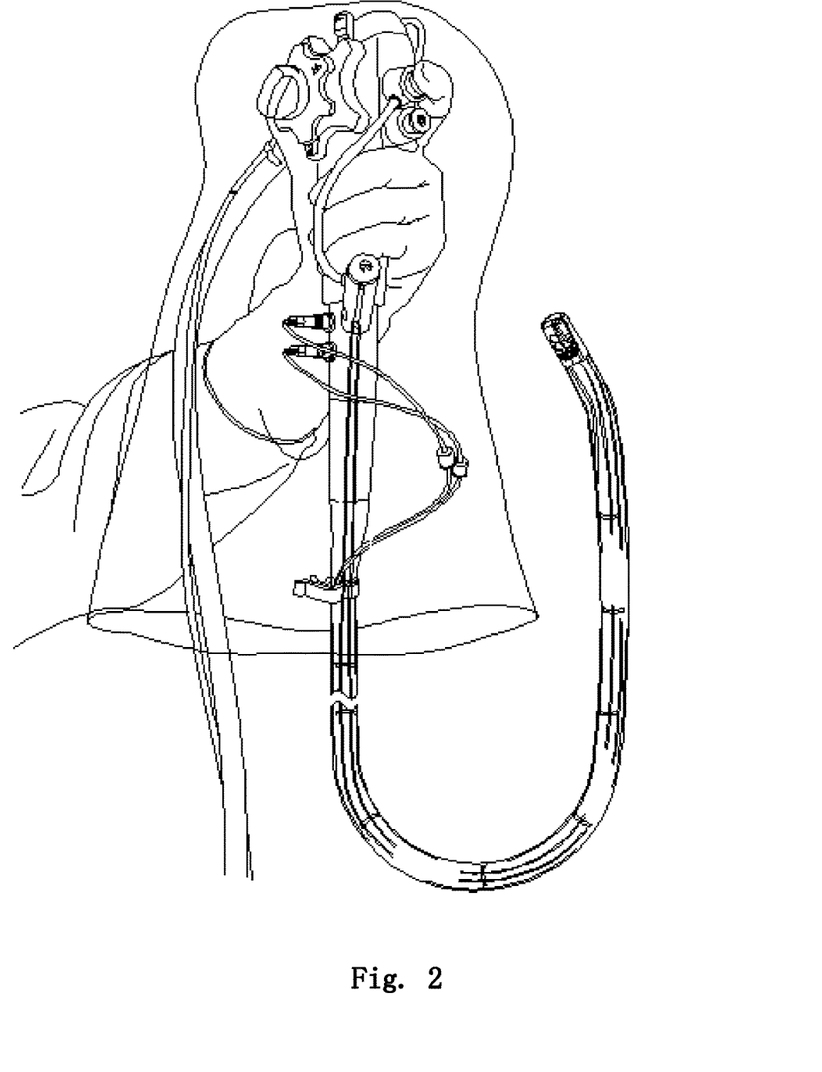
FIG. 2 is to show operation of endoscope with sheath.
Figure 3:
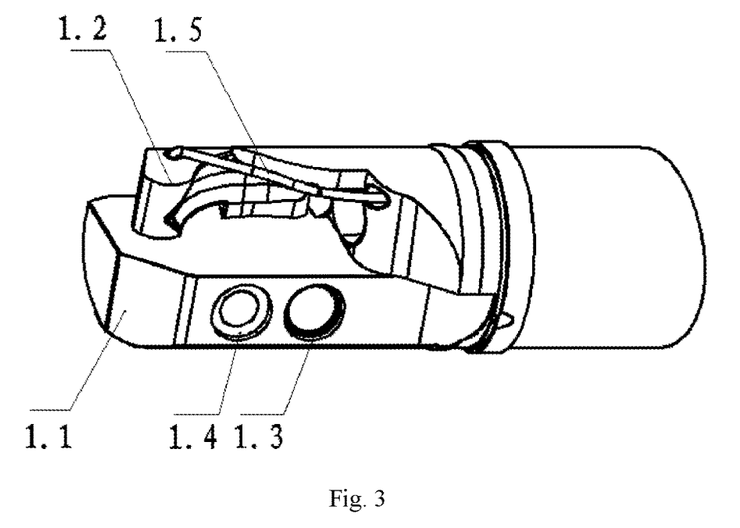
FIG. 3 is to display structures inside of the distal end portion of the shaft of endoscope.
Figure 4:
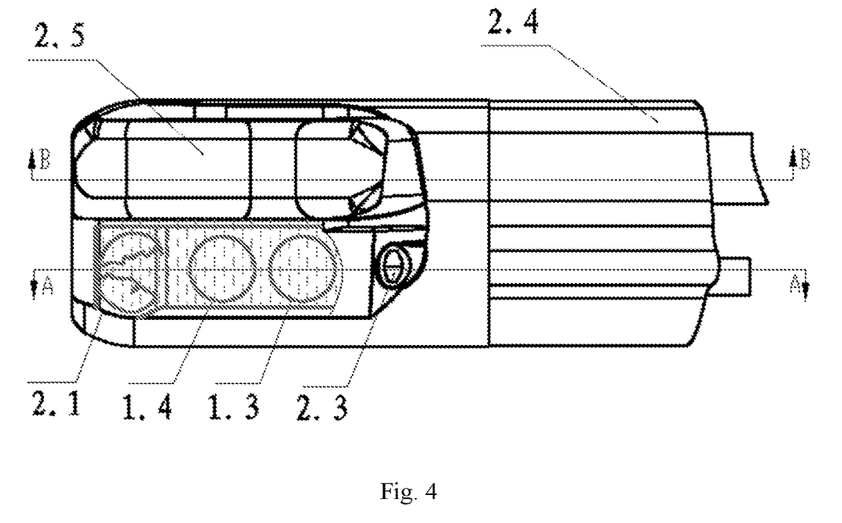
FIG. 4 is to show the assembling of the end cap and the distal end portion of the shaft of endoscope.
Figure 9:
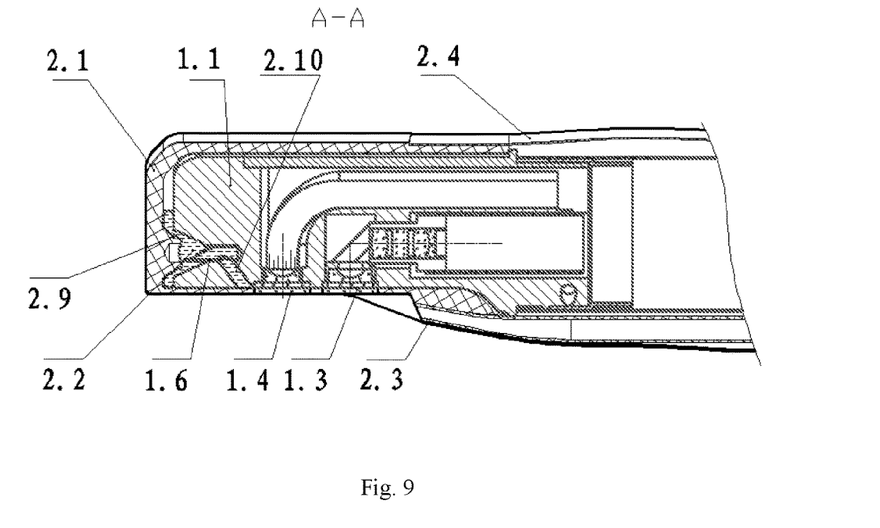
FIG. 9 is to demonstrate the finished assembling of the end cap and the distal end portion of the shaft of endoscope after the capsule become broken.
Figure 10:
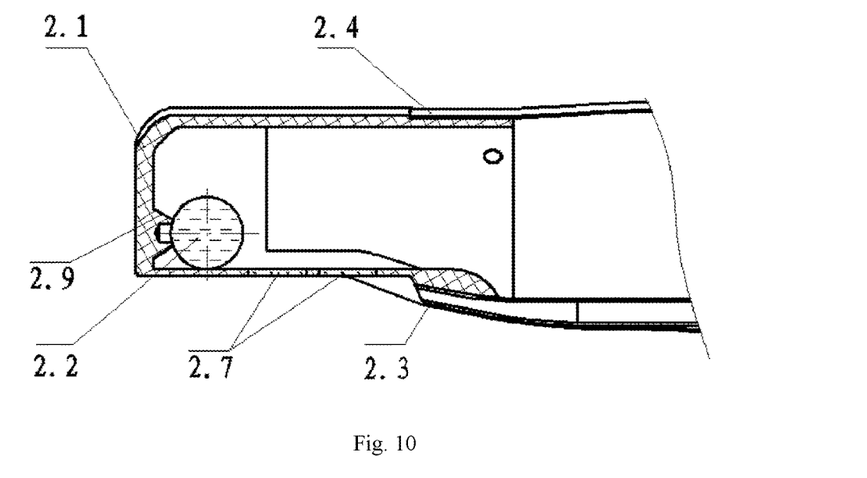
FIG. 10 is to display the structures before the capsule is pierced.
Figure 11:
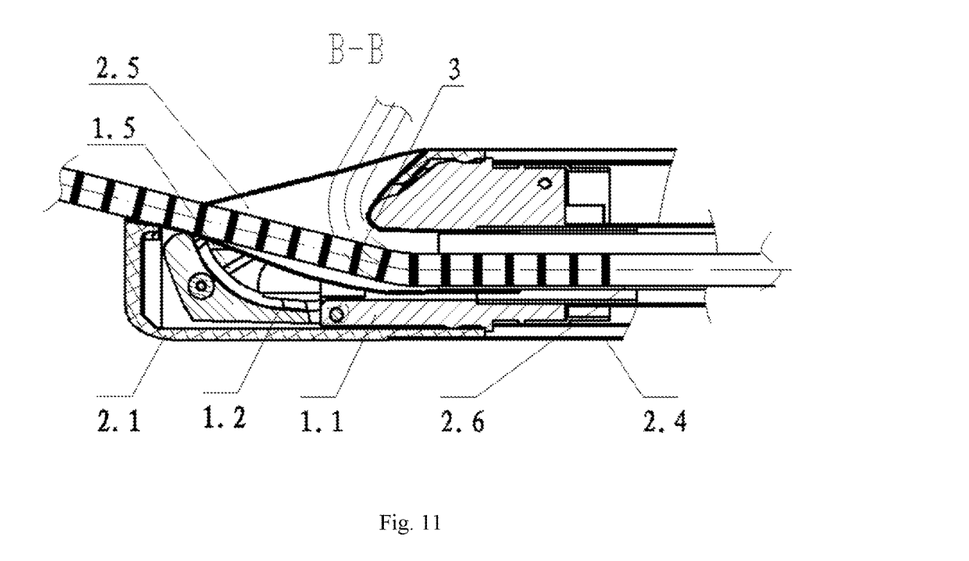
FIG. 11 is to display the structure when forceps elevator is relaxed.
Figure 12:
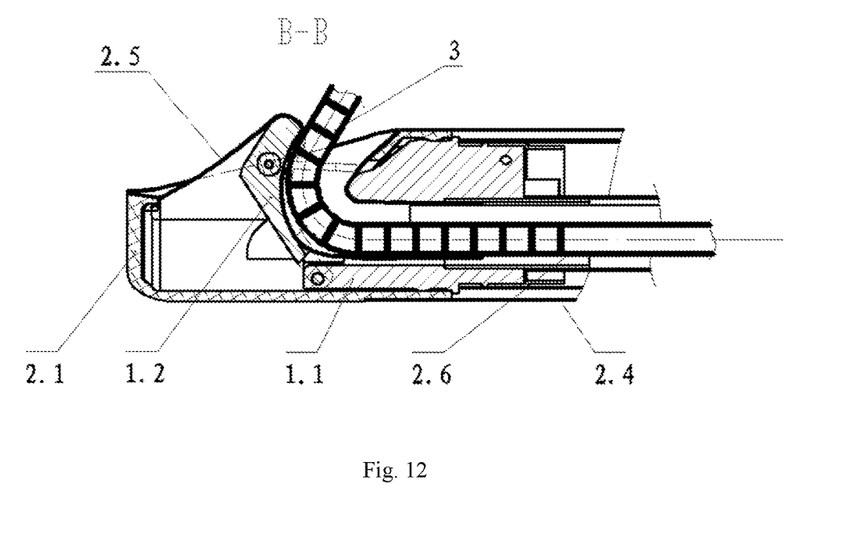
FIG. 12 is to display the soft connector and biopsy forceps while the forceps elevator is tensioned.

As shown in FIG. 1-13, this invention comprises two parts: one is modified endoscope 1, as shown in FIG. 3, wherein there is an elongated slot on the distal end portion 1.1 of the shaft of the endoscope with a forceps elevator 1.2 disposed inside; another part is the disposable component 2, as shown in FIG. 4-13, which covers the endoscope to protect it from being contaminated, including both the cuff 2.4 and the end cap 2.1 covering the out surface, as shown in FIG. 11-12, the disposable biopsy channel 2.6 connecting with the end cap, covering totally the endoscope 1 on both inside and outside. There is the capsule 2.2 filled with transparent liquid being provided in between the end cap 2.1 and the distal end portion 1.1 of the shaft of the endoscope, which will become broken under a cooperative action of the end cap 2.1 and the distal end portion 1.1 of the shaft of the endoscope. After the capsule 2.2 being broken, the transparent liquid contained in the capsule 2.2 will fill the space between the end cap 2.1 and the observation window 1.3 and the optical illumination window 1.4 located in the distal end portion 1.1 of the shaft of the endoscope.

DESCRIPTIONS BASED ON DRAWINGS

Figure 5:
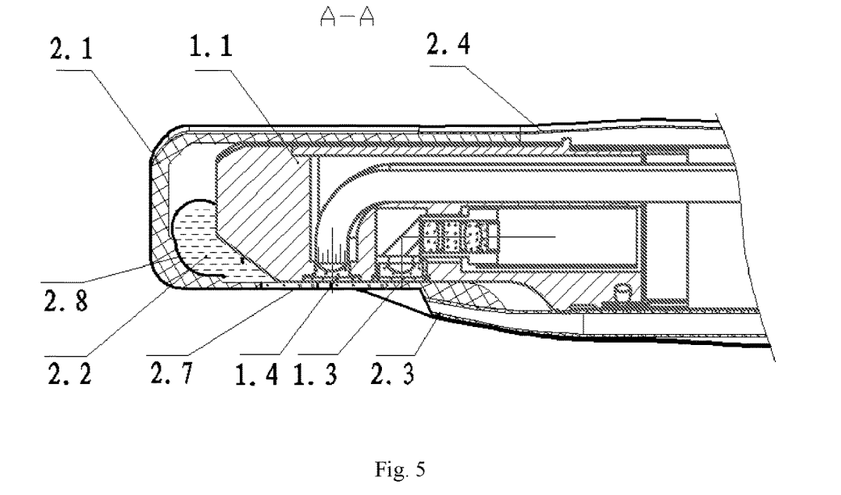
FIG. 5 is to show how the capsule gets broken during assembling of the end cap and the distal end portion of the shaft of endoscope.
Figure 13:
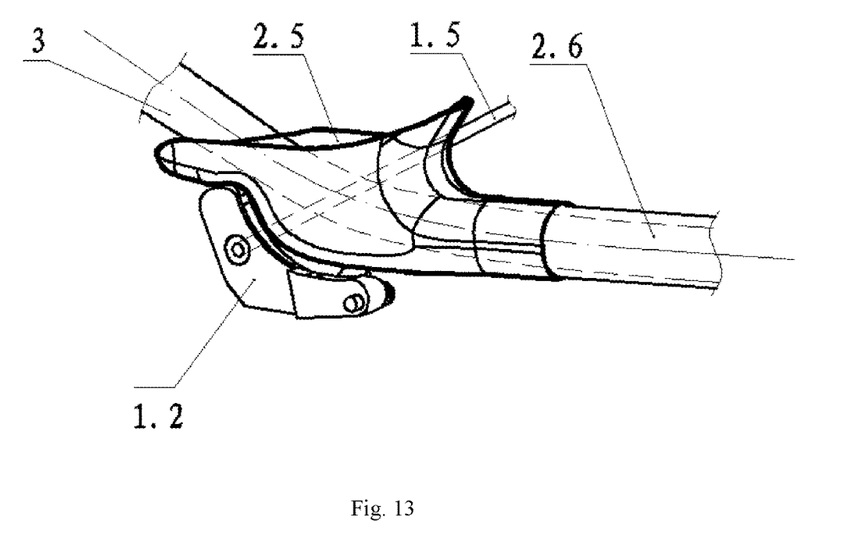
FIG. 13 is to display how forceps and soft connector coordinate with each other.

As shown in FIG. 4-13, the disposable component 2 comprises the end cap 2.1, the air/water tubes 2.3, the cuff 2.4, soft connector 2.5 and disposable biopsy channel 2.6, wherein the end cap 2.1 is assembled outside of the distal end portion 1.1 of the shaft of endoscope, the end cap 2.1 is made of transparent elastic material. As shown in FIG. 11-12, there is an elongated slot in a shape consistent with the shape of the surgical channel on the distal end portion 1.1 of the shaft of the endoscope, a soft connector 2.5 is disposed in the elongated slot, an outer edge of a large opening of the soft connector 2.5 is sealingly bonded to an inner side of the elongated slot on the end cap 2.1, and a small opening of the soft connector 2.5 is covered on the disposable biopsy channel 2.6. The opening side of the end cap connects with the cuff 2.4, by which the outer surface of the endoscope got covered. Between the cuff 2.4 and the distal end portion 1.1 of the shaft of endoscope, there is air/water channel 2.3 disposed. As shown in FIG. 5, there is the capsule 2.2 filled with transparent liquid being provided in between the end cap 2.1 and the distal end portion 1.1 of the shaft of the endoscope; as shown in FIG. 11-13, the biopsy forceps 3 extends through the disposable biopsy channel 2.6 and the distal end portion 1.1 of the shaft of endoscope, reaching the soft connector 2.5 through the soft connector 2.5.

As shown in FIG. 3-13, the endoscope 1 comprise: the distal end portion 1.1 of the shaft of endoscope, the forceps elevator 1.2 and the controlling wire 1.5. There is an opening provided on a side of the distal end portion 1.1 of the shaft of the endoscope, wherein the forceps elevator 1.2 is disposed in the foregoing opening, and the forceps elevator 1.2 is operable via the controlling wire 1.5. As shown in FIG. 11-13, when the forceps elevator 1.2 and the controlling wire 1.5 are in relaxed status, the forceps elevator 1.2 doesn't interact with the soft connector 2.5, and the biopsy forceps 3 extends obliquely from the soft connector 2.5 via the elongated openings on the end cap 2.1. However, when the controlling wire 1.5 lifts the forceps elevator 1.2, the soft connector 2.5 will be transformed and the disposable biopsy channel 2.6 will also be pushed to lift up across the soft connector 2.5, which indirectly controls the lifting direction of the biopsy forceps 3 for tissue biopsy operation.

In this invention, to improve the light transmission and illumination, the illumination windows are provided on the end cap 2.1, locating at lower side 2.7 which is inferior of the places corresponding to the observation window 1.3 and the illumination window 1.4 on the distal end of endoscope 1.1. The illumination windows are sealed with optical materials, of which the shapes conform to the observation window 1.3 and illumination window 1.4 on the distal end of endoscope 1.1.

In this invention, the capsule containing transparent fluid are placed in different places on the inner wall of the end cap 2.1, which also will become broken due to different ways of co-fraction.

Example 1

Figure 6:
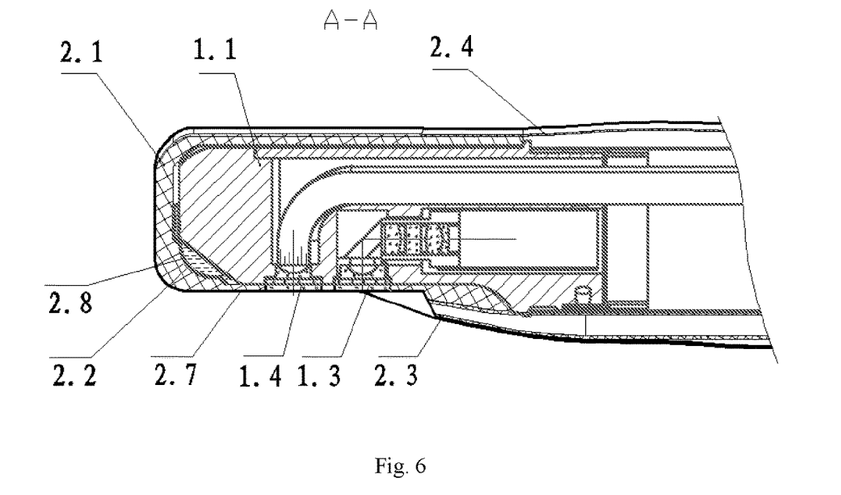
FIG. 6 is to show the finished assembling of the end cap and the distal end portion of the shaft of endoscope after the capsule gets broken.
Figure 7:
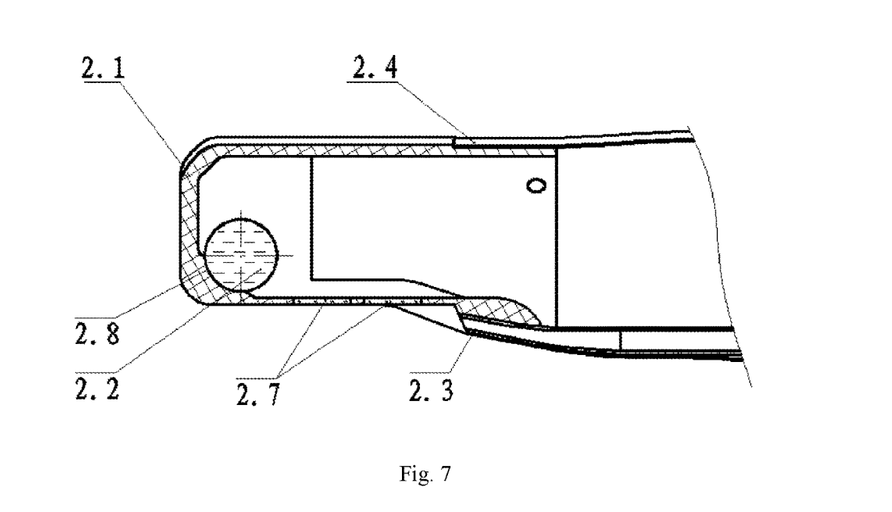
FIG. 7 is to demonstrate the structures before the capsule become broken.

As shown in FIG. 5-7, in this case, an inclined surface is formed at a location connecting the front end face of the end cap 2.1 and the lower side 2.7 of the end cap 2.1, a recess 2.8 is formed on the inclined surface, the capsule 2.2 is disposed in the recess 2.8 and fixed with adhesion. The capsule 2.2 will be broken by way of a cooperative action of the inclined surface formed at the location connecting the front-end face of the end cap 2.1 and the lower side 2.7 and the distal end portion 1.1 of the shaft of the endoscope. As shown in FIG. 5-6, an inclined surface is formed at the location on the front-end face of the object lens side of the distal end portion of the shaft of endoscope 1.1 near the lower side 2.7. When the distal end portion 1.1 of the shaft of endoscope interacts with the end cap 2.1 to crush the capsule 2.2 containing transparent fluid 2, the inclined surface inclined surface formed at the location connecting the front end face of the end cap 2.1 and the lower side 2.7 will cooperatively act with the inclined surface on the distal end portion 1.1 of the shaft of endoscope, so that the capsule 2.2 containing transparent fluid will become broken and the transparent liquid will flow along the lower side 2.7 to fill the space between the light window on the end cap 2.1 and the observation window 1.3 and optical illumination window 1.4 on the distal end portion 1.1 of the shaft of the endoscope.

Example 2

Figure 8:
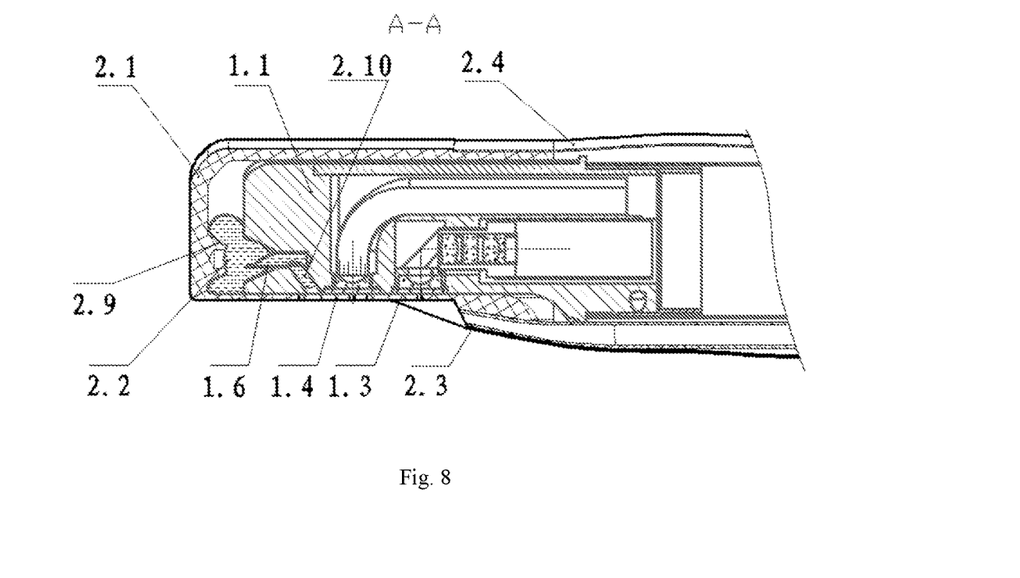
FIG. 8 is to show how the capsule gets pierced by hollow needle during assembling of the end cap and the distal end portion of the shaft of endoscope.

As shown in FIG. 8-10, in this case, the difference of this case from example 1 is that: a boss 2.9 is provided on the inner wall of the front end face of the end cap 2.1, a hollow needle 1.6 is provided on the front end face of the distal end portion 1.1 of the shaft of endoscope. The capsule 2.2 containing transparent fluid is fixed on the boss 2.9 with adhesion and will be pierced by the hollow needle 1.6.

As shown in FIG. 8-9, a hollow needle 1.6 is provided on the same side with the observation window 1.3 and the illumination window 1.4 on the distal end portion 1.1 of the shaft of endoscope. A conical recess is provided on the distal end portion 1.1 of the shaft of endoscope coaxially located with the capsule 2.2 containing transparent fluid. A blind hole and a through hole at the bottom of the conical recess, wherein the blind hole connects the conical recess on one end, and the through hole 2.10 on the other end. The transparent fluid will flow along the lower side 2.7 of the end cap 2.1 via the through hole. The hollow needle 1.6 is mounted in the blind hole with its pinpoint facing outside, and the pinpoint of the hollow needle 1.6 is not higher than the large end surface of the conical recess to ensure the hollow needle 1.6 remain inside of the conical recess. A through hole 2.10 is provided at the tail end of the hollow needle 1.6, which obliquely points towards the plane where the observation window 1.3 and optical illumination window 1.4 are located on the distal end portion 1.1 of the shaft of endoscope, formed by pinpointing. When the end cap 2.1 assembles with the end portion 1.1 of the shaft of endoscope, the capsule 2.2 containing transparent fluid will become broken through piercing by the hollow needle 1.6 on the end portion 1.1 of the shaft of endoscope, and the transparent fluid will be released to flow along the canal inside the hollow needle 1.6 to the tail end of the hollow needle 1.6, then finally arrive and fill the space between the end cap 2.1 and the observation window 1.3 and optical window 1.4 on the distal end portion 1.1 of the shaft of the endoscope via the through hole 2.10.

What is claimed is:

1. An endoscope assembly comprising:
   an endoscope with an illumination window adjacent to an observation window situated along a lateral side of a distal end portion, wherein the distal end portion further comprises an elongated slot to accommodate a forceps elevator; and
   a sheath to envelope and to engage the endoscope further comprises:
   an end cap fitting around the distal end portion of the endoscope;
   a capsule secured to an inner wall of the end cap, the capsule is configured to rupture when the end cap engages the endoscope thereby releasing a transparent liquid within the capsule so as to immerse the illumination window and the observation window enveloped within the sheath;
   a soft connector bonded to the end cap at a first end covering the elongated slot, and at a second end to an outer surface of a biopsy channel, wherein the soft connector further comprises an opening allowing the biopsy channel to pass through;
   an air/water tube; and
   a cuff to secure the sheath to the endoscope.

2. The endoscope assembly of claim 1 wherein the sheath is made of disposable material.

3. The endoscope assembly of claim 1 wherein the capsule is secured within a recess along an inner surface of the end cap.

4. The endoscope assembly of claim 1 where the capsule is ruptured, when the end cap engages the distal end portion of the endoscope, to release the transparent liquid so as to immerse the illumination window and the observation window enveloped within the sheath.

5. The endoscope assembly of claim 1 wherein the distal end portion of the endoscope further comprises an inclined surface to facilitate flow of the transparent liquid to the illumination window and the observation window.

6. The endoscope assembly of claim 1 wherein the forceps elevator is couple with a control wire to manipulate angular rotation of the biopsy channel.

7. The endoscope assembly of claim 1 wherein the biopsy channel is bonded and sealed at a predetermined location as it passes through the soft connector.

8. The endoscope assembly of claim 1 wherein the soft connector is made of flexible material to accommodate movements of the biopsy channel while maintaining its structural integrity when engaged with the endoscope.

* * * * *